United States Patent [19]

Sachse

[11] Patent Number: 5,407,435
[45] Date of Patent: Apr. 18, 1995

[54] URETER TUBES WITH CLAMPING MANDRIN

[76] Inventor: Hans-Ernst Sachse, Lerchenstr. 55, 8500 Nuernberg 90, Germany

[21] Appl. No.: 124,509

[22] Filed: Sep. 21, 1993

Related U.S. Application Data

[63] Continuation of Ser. No. 714,369, Jun. 12, 1991, abandoned, which is a continuation of Ser. No. 462,221, Jan. 9, 1990, abandoned.

[30] Foreign Application Priority Data

Jan. 12, 1989 [DE] Germany ................ 39 00 738.3

[51] Int. Cl.⁶ ............................................. A61M 25/00
[52] U.S. Cl. ........................................ 604/170; 604/8; 604/280
[58] Field of Search ................. 604/8, 158, 164, 165, 604/170, 264, 280, 281

[56] References Cited

U.S. PATENT DOCUMENTS

| | | | |
|---|---|---|---|
| 3,419,010 | 12/1968 | Williamson | 604/170 |
| 4,571,239 | 2/1986 | Heyman | 604/170 |
| 4,610,657 | 9/1986 | Densow | 604/8 |
| 4,713,058 | 12/1987 | Sachse | 604/165 |
| 4,787,884 | 11/1988 | Goldberg | 604/8 |
| 4,834,702 | 5/1989 | Rocco | 604/170 |
| 4,834,707 | 5/1989 | Evans | 604/164 |
| 4,834,709 | 5/1989 | Banning et al. | 604/170 |
| 4,874,360 | 10/1989 | Goldberg et al. | 604/8 |
| 4,887,996 | 12/1989 | Bengmark | 604/281 |
| 4,931,037 | 6/1990 | Wetterman | 604/8 |
| 4,957,479 | 9/1990 | Roemer | |
| 4,963,129 | 10/1990 | Rusch | 604/8 |
| 4,986,814 | 1/1991 | Burney et al. | 604/164 |
| 5,074,849 | 12/1991 | Sachse | 604/280 |

FOREIGN PATENT DOCUMENTS

| | | |
|---|---|---|
| 3640745 | 11/1985 | Germany . |
| 8614013.2 | 8/1986 | Germany . |
| 8801101.1 | 4/1988 | Germany . |
| 3714839 | 11/1988 | Germany . |
| 3837196 | 8/1989 | Germany . |
| 3824244 | 1/1990 | Germany . |
| 3836136 | 4/1990 | Germany . |

Primary Examiner—Ralph A. Lewis
Attorney, Agent, or Firm—Keil & Weinkauf

[57] ABSTRACT

A ureter tube with mandrin and auxiliary tube, designed so that all three elements are adapted to be connected together by different clamping means such that they functionally form an entity for the introduction process, this entity being so stable that the three elements cannot detach themselves from one another even in the case of back and forth sliding and rotational movements. Upon correct placement of the ureter tube, the connection between ureter tube and auxiliary tube is released upon removal of the mandrin, the auxiliary tube is also removed and the ureter tube is left in the body, with the curvatures of its tip and its end lying between renal pelvis and bladder.

13 Claims, 9 Drawing Sheets

URETER TUBES WITH CLAMPING MANDRIN

This application is a continuation of application Ser. No. 07/714,369, now abandoned filed on Jun. 12, 1991 which is a continuation of Ser. No. 07/462,221, filed on Jan. 9, 1990, now abandoned.

In the splinting of the ureter, ureter tubes have proven to be very useful because of an inherent curvature in the tip of the ureter tube which prevents the ureter tube from slipping out of the renal pelvis once it has been introduced. A second inherent curvature in the ureter tube tip prevents the ureter tube end from being completely pulled out of the bladder and into the ureter from the direction of the bladder.

For their introduction into the ureter, these ureter tubes, otherwise known as "pig tail" tubes, because of their curved shape, must be straightened by a relatively stiff but still flexible mandrin. This mandrin also serves as a guide for an auxiliary tube which is needed for sliding the ureter tube end into the bladder. As a rule, the curved tip of the ureter tube lies in the renal pelvis, and the curved end of the ureter tube lies in the bladder.

The placement of the ureter tube takes place with the aid of a cystoscope. The surgeon introduces the cystoscope through the urethra, into the bladder, optically locates the ureter outlet and then shoves the tip of the ureter tube through the ureter outlet into the ureter. He subsequently slides the ureter tube in an upward direction toward the kidney until the ureter tube tip comes to lie in the renal pelvis. This process is controlled with the aid of X-rays. For this introduction process into the ureter, the tip and end sections of the ureter tube must be straightened by the mandrin. In order to place the ureter tube, which is somewhat longer that the ureter, in such a way that the curvature in the tip range lies in the renal pelvis and the curvature in the range of the ureter tube end lies in the bladder, a second little tube, known as an auxiliary tube, is needed. With this auxiliary tube, which also is slipped onto the mandrin shaft, the ureter tube can be advanced first through the cystoscope shaft and then into the ureter until merely the curved end of the ureter tube protrudes from the ureter outlet. After the ureter tube has been properly put in place, the mandrin is withdrawn from the ureter tube and the auxiliary tube. Subsequently, the auxiliary tube is removed from the bladder and the urethra.

In the systems which were commercially available in the past, the mandrin does not have a close contact with the ureter tube and with the auxiliary tube, but it is freely movable in their lumen. Therefore, in commercially available systems, it is necessary, before starting the introduction, to tightly press both the end of the ureter tube and the end of the auxiliary tube against the mandrin by means of strong clamps in order to fix them for the introduction process. This clamping is performed by means of relatively large and heavy surgical clamps which impede the surgeon in his work and frequently bend the mandrin, which usually consists of metal. As the ureter tube is slid upwardly into the lower section of the ureter, the end of the ureter tube disappears in the cystoscope shaft. At this point the clamp placed at the ureter tube end must be removed thus releasing the ureter tube and mandrin from each other. From this moment on, the ureter tube can only slide forward in the direction of the renal pelvis. Every time an attempt is made to pull the ureter tube back somewhat, or to turn it, the ureter tube detaches itself from the mandrin and quite frequently remains in the ureter and in the bladder before the tip of the ureter tube has reached the renal pelvis. When this occurs, the ureter tube after having been released from the mandrin must now be removed, by means of tweezers, in a separate procedure. Because of the irregular and constricted configuration of the ureter, these rotary movements and the pulling back of the ureter tube cannot be avoided in the sliding up of the ureter tube.

OBJECT AND SUMMARY OF THE INVENTION

It is the object of the present invention to design the ureter tube, the auxiliary tube and the mandrin in such a way that these three units form a functional entity which, for an improved introduction, makes forward as well as rearward, or rotary movements of the ureter tube possible, and upon proper placement of the ureter tube, facilitates the removal of the mandrin and the auxiliary tube.

This object is met according to the invention, in principle, by clamping the mandrin in the ureter tube, whereby the auxiliary tube, in addition to assisting the introduction process, primarily has the function to facilitate, upon placement of the ureter tube, the removal of the mandrin, with the exertion of some force, without change in the position of the ureter tube.

This clamping between ureter tube and mandrin, is brought about by the fact that the ureter tube end section 3 has a section 5 with restricted inner lumen, which firmly engages the outer shaft of mandrin 7. This section 5 which constricts the lumen of the ureter tube may be an integral part of the ureter tube wall and may consist of the same material, or this section 5, may consist of a particular firmly adhering material. If the mandrin consists of metal and is firmly fused with the constricted ureter tube section which is of plastic material, then, upon connection of one terminal of a current source 15 to the mandrin and another terminal to the body of the patient, the mandrin can be heated to the point where the plastic material of the constricted ureter tube section 5 is likewise heated, softened and the firm connection to the mandrin is released.

Figure 1:
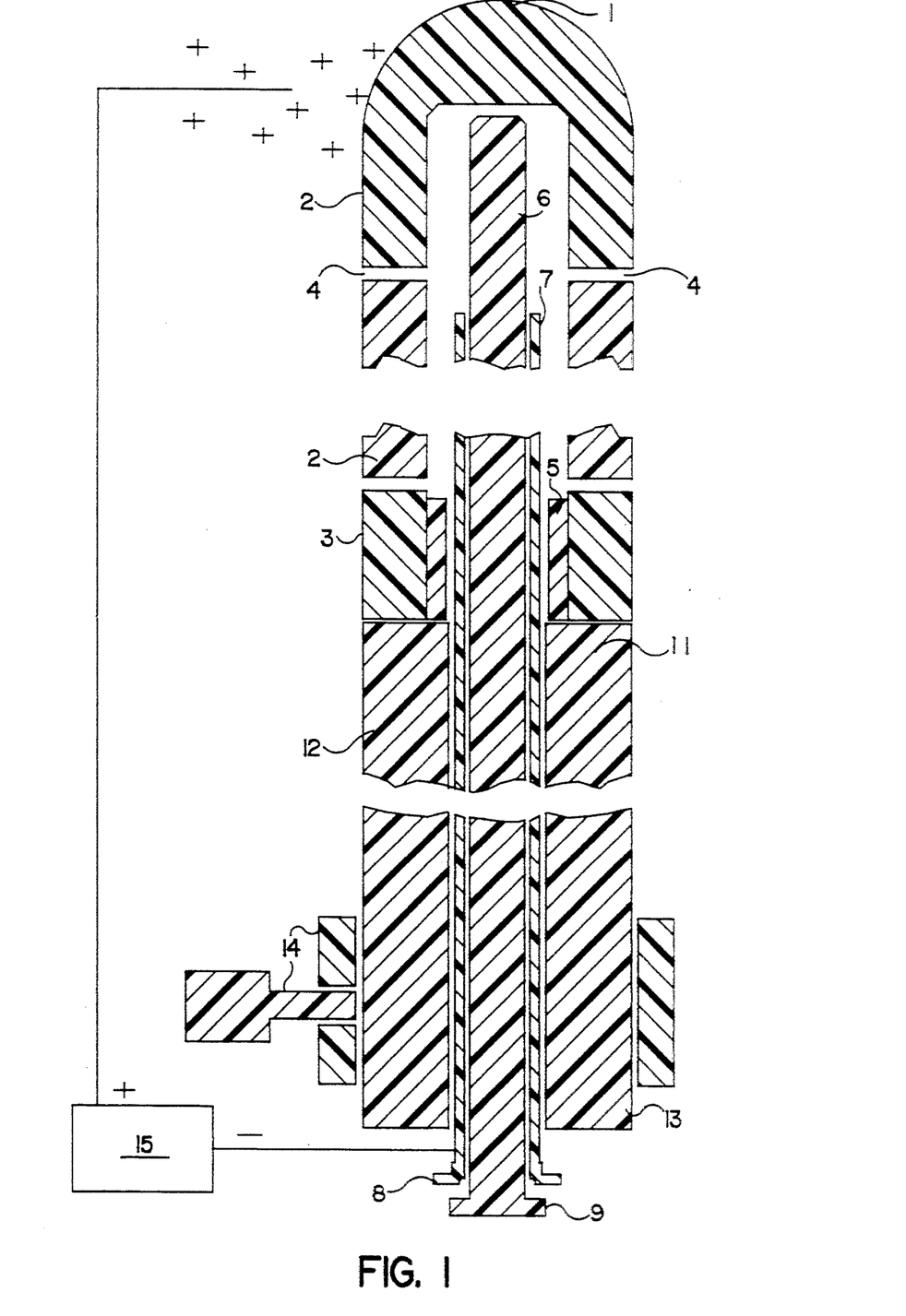
FIG. 1 is a longitudinal section through the ureter tube with a double mandrin, an auxiliary tube, a current source and a section of the ureter tube end, which constricts the lumen of the ureter tube.
Figure 8:
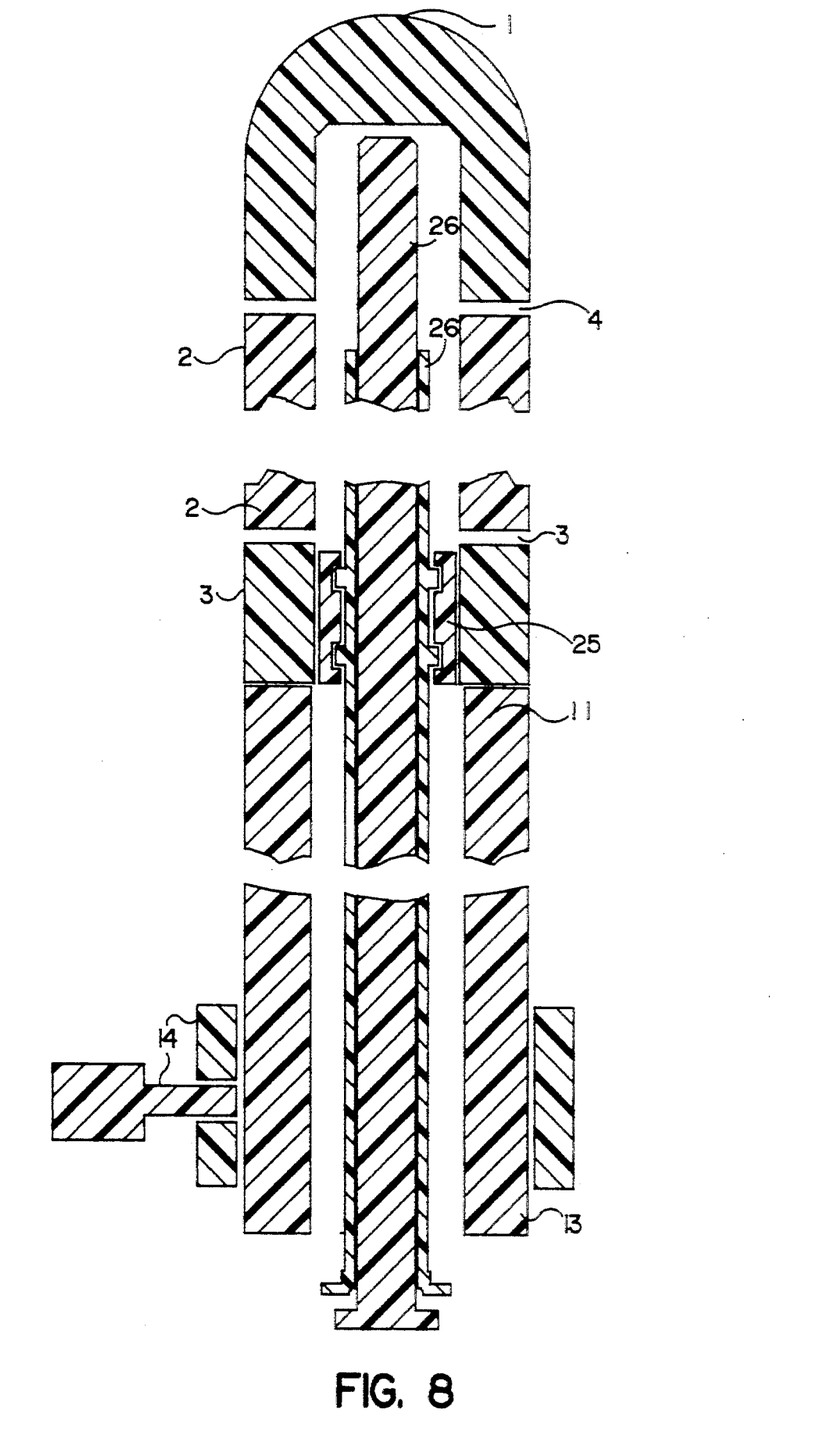
FIG. 8 is a longitudinal section through the ureter tube, the auxiliary tube and a double mandrin which has an external sleeve firmly connected therewith, with projections of the external mandrin.

In the introduction process the mandrin shaft is still reinforced by the auxiliary tube 12 which is slid upon the mandrin, this auxiliary tube in the range of the auxiliary tube end 13 being firmly pressed against the mandrin by a clamp 14. In case a double mandrin is used as represented in FIG. 1 and FIG. 8 these two figures and the remaining figures of the drawing being listed and described in greater detail hereinbelow then, by pulling mandrin 6 back to different degrees, a more or less pronounced curvature of the ureter tube tip 1 may temporarily be achieved—a process which, in case the sliding up presents difficulties, often affords advantages. A more pointed shape of the ureter tube tip can substantially facilitate the introduction of the ureter tube tip into the ureter outlet. After the ureter tube has been slid up the inner shaft 6 of the mandrin, in the case of the example of FIG. 1 can be removed and a syringe containing a contrast medium can be placed on the flange section 8 provided on the external shaft 7. The contrast medium can then exit through the drainage channels 4 of the ureter tube into the ureter and the renal pelvis to make these organs visible to X-rays. Upon correct placement of the ureter tube tip in the renal pelvis, clamp 14 at the auxiliary tube end 13 is released. The single mandrin or a double mandrin according to FIG. 1 and FIG. 8 can be completely withdrawn, with the auxiliary tube still in place, tip 11 of the auxiliary tube bearing against end 3 of the ureter tube. Subsequently, the auxiliary tube, 2, is removed.

Figure 2:
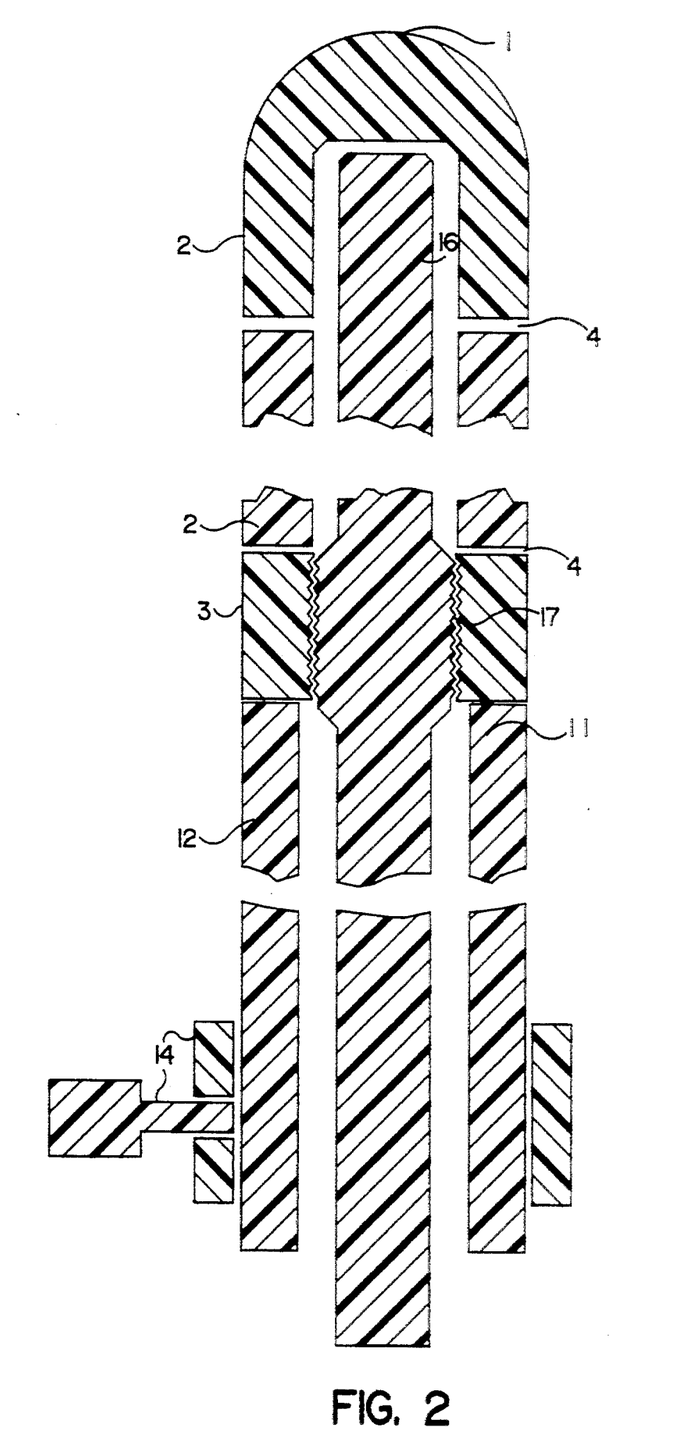
FIG. 2 is a longitudinal section through the ureter tube, the auxiliary tube and a mandrin, with the mandrin shaft having an enlargement in the range of the ureter tube end.
Figure 3:
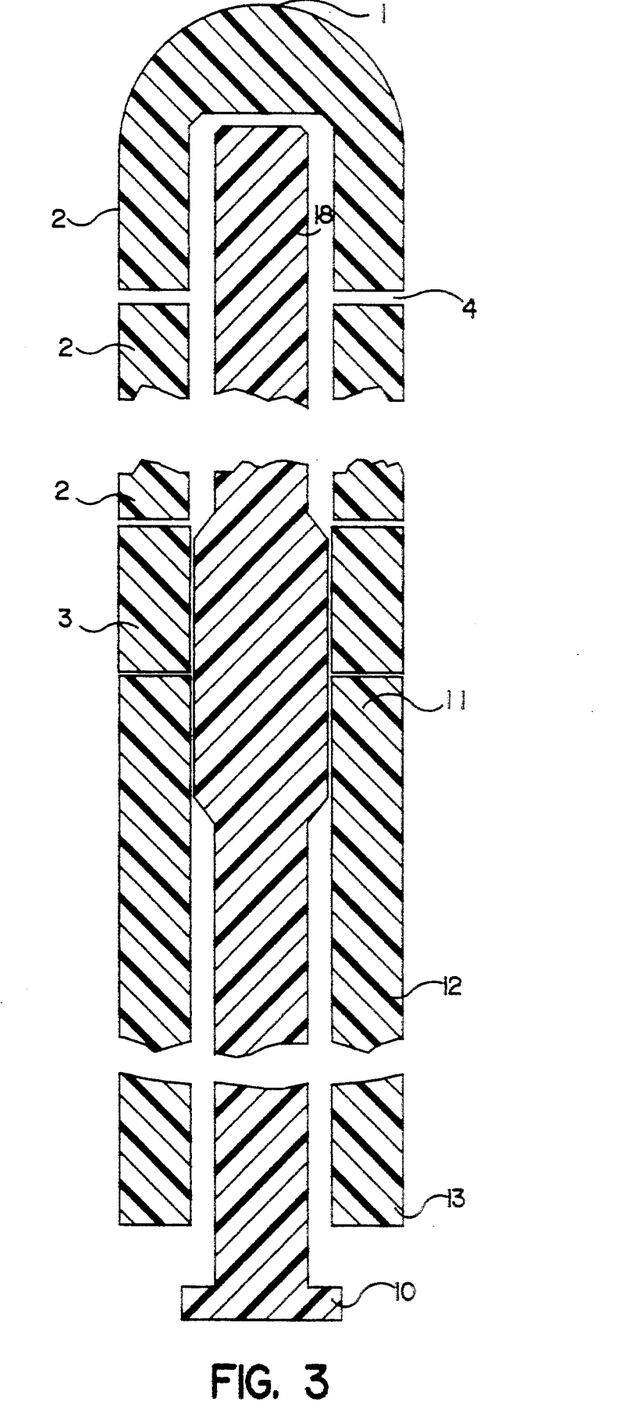
FIG. 3 is a longitudinal section through the ureter tube, the auxiliary tube and a mandrin which has an enlargement in the end range of the ureter tube as well as in the tip range of the auxiliary tube.
Figure 4:
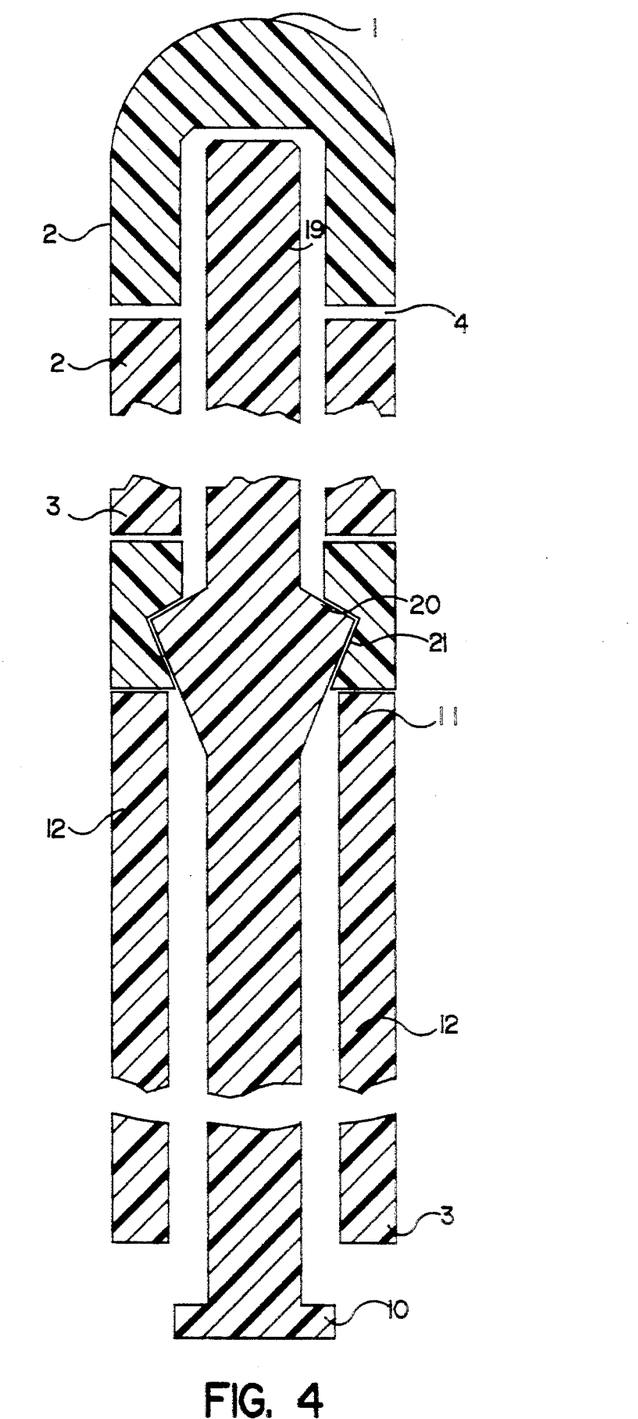
FIG. 4 is a longitudinal section through the ureter tube, the auxiliary tube and a mandrin which has a double cone-shaped enlargement while the ureter tube has a corresponding recess.
Figure 5:
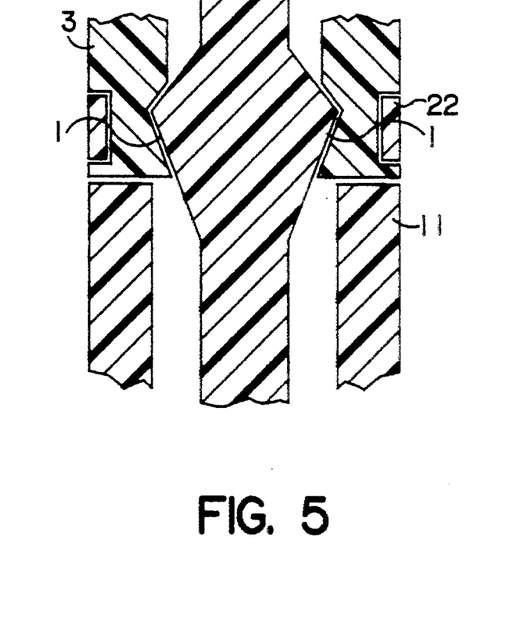
FIG. 5 is a longitudinal section through the end section of the ureter tube of FIG. 4 with a circular elastic band.
Figure 6:
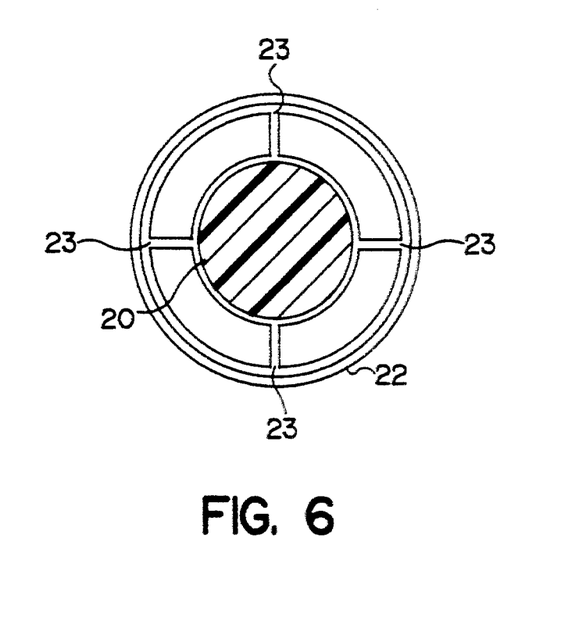
FIG. 6 is a cross-section of FIG. 4 along line I—I with cut-ins of the ureter tube end section.

According to clamping between the internal lumen,—here of uniform width throughout, of the ureter tube 5 and mandrin 16 takes place by means of a mandrin section 17 having a larger diameter in the range of the ureter tube end 3. This clamping between ureter tube and mandrin can be further enhanced by transverse or longitudinal grooves, as illustrated in FIG. 2. These grooves may be faced by a corresponding relief of the ureter tube. Also the tip range 11 of the auxiliary tube is included in the clamping operation of the mandrin, as shown in FIG. 3. As shown in FIGS. 4 to 6, mandrin shaft 19 has a double cone-shaped enlargement 20 in the range of the ureter tube end 3. This enlargement is engaged by a corresponding recess 21 of the ureter tube end into which this enlargement extends. Upon withdrawal of the mandrin the cone-shaped enlargement of the mandrin spreads the last section of the ureter tube end apart and releases the ureter tube end. In order to facilitate this process the end of ureter tube 3 may, have one or more longitudinal cuts 23 (FIG. 6). In this embodiment the lumen of the auxiliary tube must be greater than the largest diameter of the mandrin enlargement 20. Greater elasticity of this last cut-in section of the ureter tube end can be achieved in that this section is held together by an elastic ring 22, FIG. 5, which lies in a corresponding recess of the ureter tube.

Figure 7:
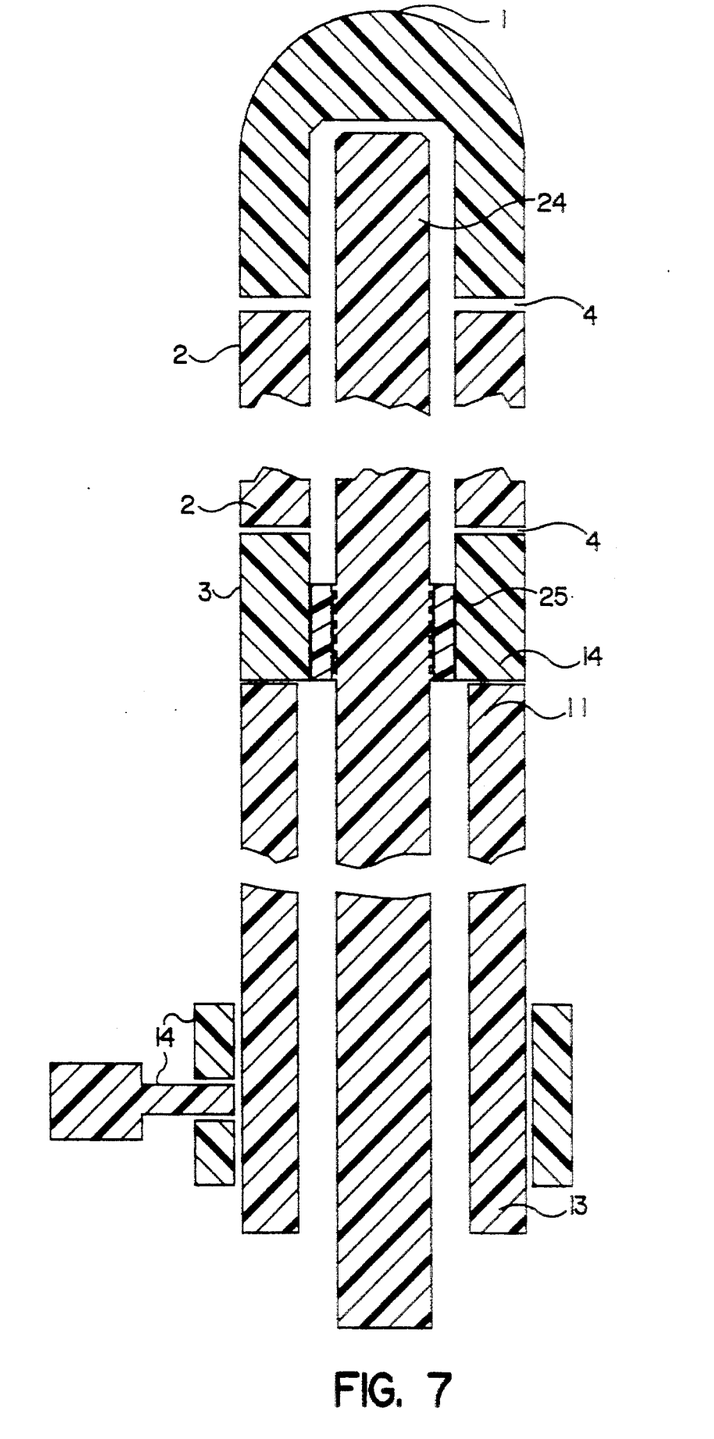
FIG. 7 is a longitudinal section through the ureter tube, the auxiliary tube and a mandrin which has an external sleeve firmly connected therewith while the mandrin has notches in this range.

According to FIG. 7, mandrin 24 has a clamping device such that mandrin 24 in the range of ureter tube end 3 includes an elastic plastic ring 25 which is firmly connected with the mandrin, this plastic ring clamping itself against the interior lumen of the ureter tube. A firmer connection between mandrin 24 and plastic ring 25 is brought about by scoring of the mandrin 24 by projections of the mandrin 26. This mechanical connection may be enhanced by adhesive connections, and this is indispensable particularly in case of a smooth mandrin surface.

Figure 9:
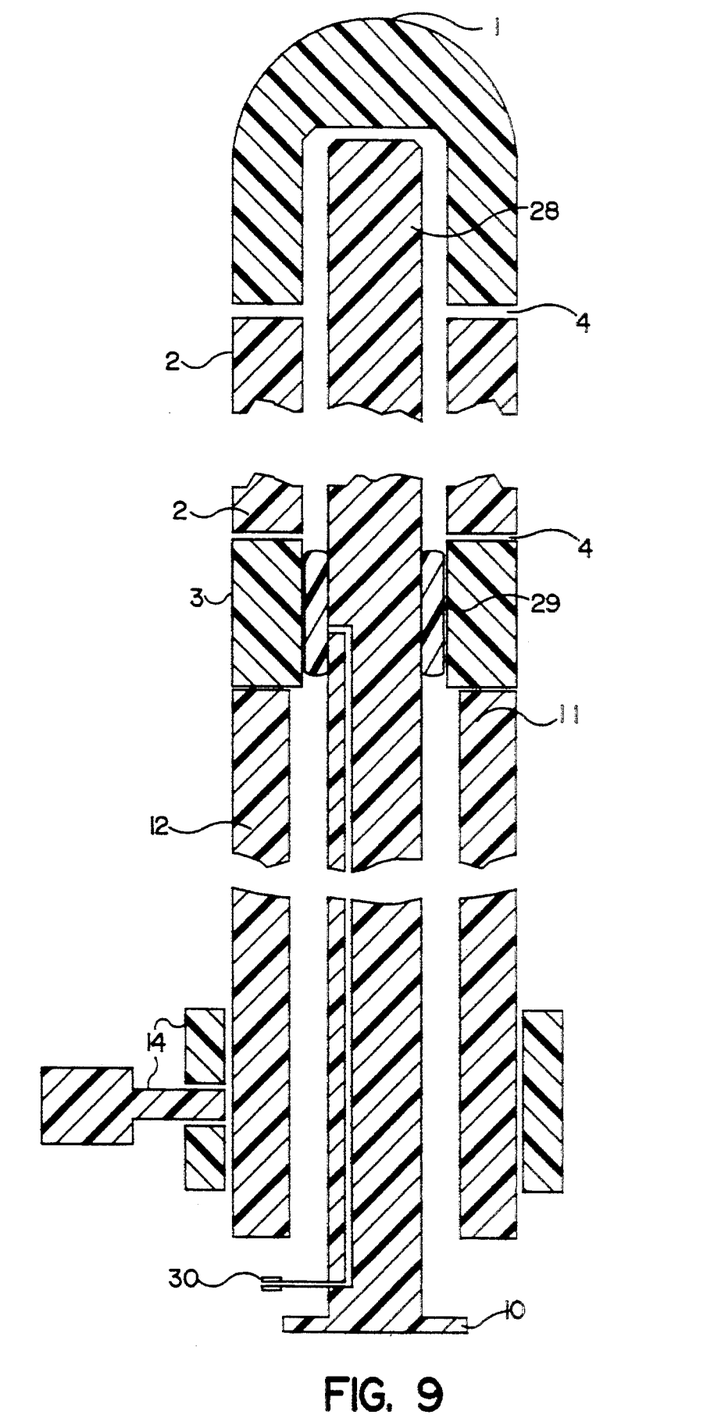
FIG. 9 is a longitudinal section through the ureter tube, an auxiliary tube and a mandrin with a short sleeve which can be blown up.

According to FIG. 9 the clamping takes place by means of an expandible sleeve of the mandrin. Thus in the case of mandrin 27 a sleeve 28 which is fillable through the filling channel 29 is provided in the end range of the ureter tube.

Figure 10:
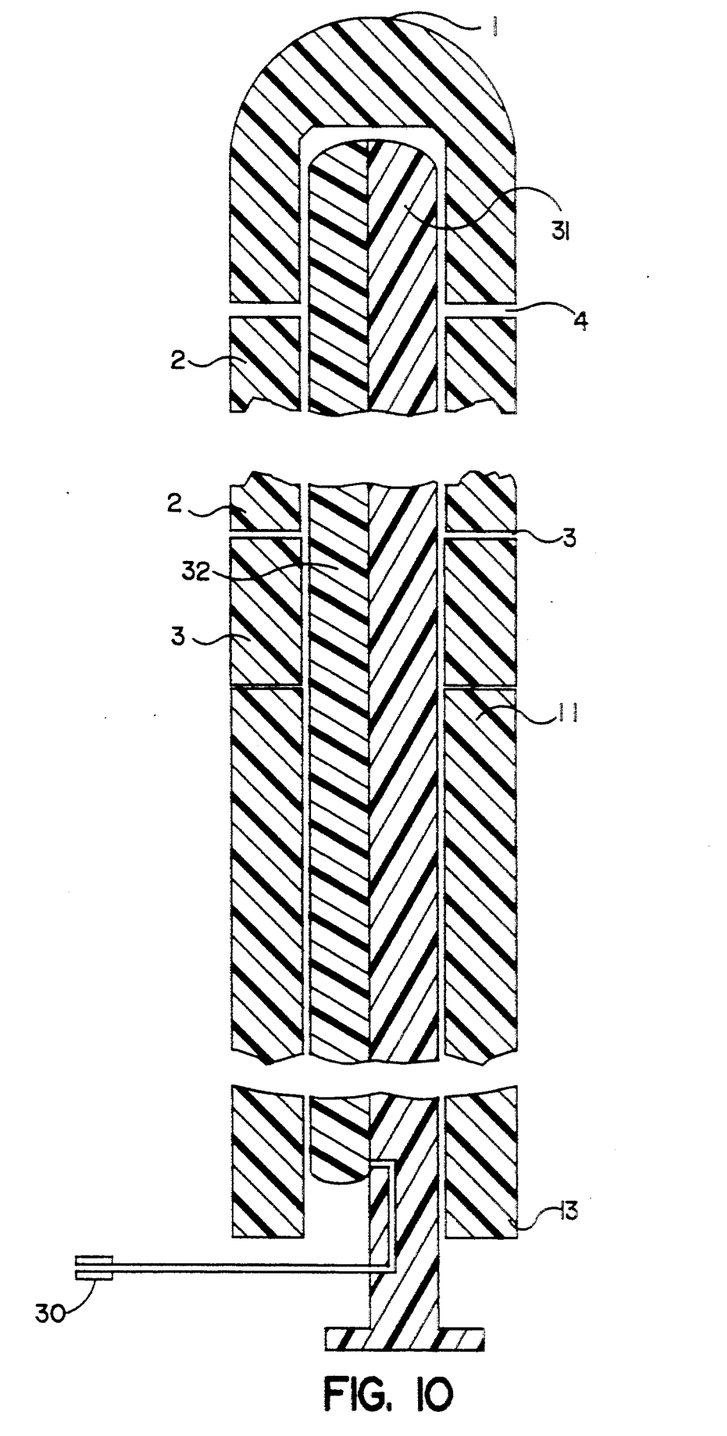
FIG. 10 is a longitudinal section through the ureter tube, an auxiliary tube and a mandrin with an expandible sleeve of almost the entire length.

In similar fashion clamping can, of course, take place in any other range, including the tip range 1 of the ureter tube. According to FIG. 10, the clamping is brought about by means of a sleeve 31 of mandrin 30, which extends almost over the entire length of the ureter tube and auxiliary tube.

BRIEF DESCRIPTION OF THE DRAWINGS

The subject of the invention is illustrated and will be described with the aid of FIGS. 1 to 10 in which.

DETAILED DESCRIPTION OF THE PREFERRED EMBODIMENTS

FIG. 1 shows a longitudinal section through the ureter tube with the sections 1,2,3 and with the drainage channels 4, the interior shaft of the mandrin 6, the mandrin exterior shaft 7 having a syringe connection flange 8 and the hand piece 9. Such double mandrins are commercially available and they usually consist of an elastic metal alloy. The clamping between mandrin exterior shaft 7 and the end of the ureter tube 3 takes place by means of the lumen-constricting section 5. By means of clamp 14 the end of the auxiliary tube 13 is firmly pressed against the mandrin exterior shaft 7. Current source 15 is connected to the metallic mandrin exterior shaft 7 and the surface of the body.

In FIG. 2 there is shown a longitudinal section through the ureter tube with an interior lumen of identical width in all sections 1-3. The clamping here takes place through the enlargement 17 of mandrin 16. The clamping action is here enhanced by means of transverse grooving of the enlargement and of the interior wall of the ureter tube.

In FIG. 3 there is shown a longitudinal section through the ureter tube, mandrin 18 and the auxiliary tube, wherein in addition to the clamping in the end section of the ureter tube 3 also a clamping in the tip range of auxiliary tube takes place.

FIG. 4 is a longitudinal section through the ureter tube, mandrin 19 and the auxiliary tube, the mandrin 19 having in the end range of ureter tube 3 a double cone-shaped enlargement 20 which extends into a corresponding recess 21 of the ureter tube wall. The interior lumen of auxiliary tube 11 in this case is larger than the largest diameter of the mandrin enlargement 20.

FIG. 5 again represents the end section of the ureter tube of FIG. 4, the exterior wall of the end section 3 of the ureter tube having an annular recess which accommodates the elastic band 22, which latter circularly surrounds this section.

FIG. 6 shows a cross section according to Section I—I of FIG. 5. In this embodiment the end section of the ureter tube is divided in four places with the longitudinally extending cut-ins 23. This divided section is held together by the circularly extending band 22.

FIG. 7 shows a longitudinal section through the ureter tube, the mandrin 24 and the auxiliary tube, the mandrin 24 in the end range 3 of the ureter tube having a sleeve 25 which is firmly connected with the mandrin and the adherence to the mandrin shaft is enhanced by notching of the latter.

FIG. 8 shows a longitudinal section through the ureter tube, the double mandrin 26 and the auxiliary tube, the double mandrin 26 in the end range 3 of the ureter tube having a sleeve which is firmly connected with the mandrin, the adherence of the sleeve to the mandrin outer shaft being enhanced by projections of the same.

FIG. 9 shows a longitudinal section through the ureter tube, mandrin 28 and the auxiliary tube, the mandrin 28 in the end range of the ureter tube having an expandible sleeve 29 which is firmly placed thereon, the sleeve being blown up with a liquid or a gas through the filling channel 30.

What is claimed is:

1. A ureter tube arrangement comprising: a ureter tube having a lumen with an inner surface and an inner diameter, a proximal end, and a distal end, at least the distal end having an inherent curvature; an auxiliary tube having a lumen, a proximal end, and a distal end, the distal end of the auxiliary tube being aligned with and abutting the proximal end of the ureter tube, both the ureter tube and the auxiliary tube being made of an elastic plastic material; a flexible double mandrin disposed within the lumen of the ureter tube and the lumen of the auxiliary tube, the flexible double mandrin having a proximal end, a distal end, an inner shaft, and an outer shaft having an outer surface and an outer diameter, the flexible double mandrin being slidable in the lumens of the ureter tube and auxiliary tube, and capable of straightening the inherent curvature of the ureter tube, the advancing of the flexible double mandrin thus causing the advancement of the ureter tube in the ureter; and at least one engaging means provided substantially at the proximal end of the ureter tube for releasably clamping the ureter tube and the outer shaft of the flexible double mandrin together so as to cause back-and-forth and rotational movement of the ureter tube in response to back-and-forth and rotational movement of the outer shaft of the flexible double mandrin, the engaging means being produced by clamping in a limited area, the inner surface of the lumen of the ureter tube to the outer surface of the outer shaft of the flexible double mandrin positioned within the lumen of the ureter tube by a) reduction of the diameter of the lumen of the ureter tube or b) increasing the diameter of the outer shaft of the flexible double mandrin, which clamping is releasable by withdrawing the outer shaft of the flexible double mandrin from the lumen of the ureter tube.

2. An arrangement as claimed in claim 1, wherein the outer shaft of the mandrin is provided with an inflatable sleeve, and wherein means are provided for blowing said sleeve up by way of said mandrin.

3. An arrangement as claimed in claim 2, wherein said inflatable sleeve extends over at least a major portion of the length of the outer shaft of the mandrin.

4. An arrangement as claimed in claim 1, wherein the outer shaft of the mandrin, at least in the proximal range of said ureter tube, has a section of enlarged diameter, tightly engaging the inner wall of the ureter tube.

5. An arrangement as claimed in claim 1, wherein the inner surface of the lumen of the ureter tube in the range of the tight engagement with the outer shaft of the mandrin has an uneven surface.

6. An arrangement as claimed in claim 1, wherein the outer surface of the outer shaft of the mandrin in the range of tight engagement with the ureter tube has an uneven surface.

7. An arrangement as claimed in claim 1, wherein said arrangement also includes an auxiliary tube which is slid over the proximal end of the mandrin, and wherein the outer shaft of the mandrin in the proximal range of the ureter tube and in the distal range of the auxiliary tube has a section of enlarged diameter which tightly engages the inner wall of the ureter tube and the auxiliary tube.

8. An arrangement as defined in claim 7, wherein said engaging means includes a section of greater wall thickness provided on said ureter tube in the range of the proximal end of said tube.

9. An arrangement as defined in claim 8, wherein said ureter section is integral with said tube.

10. An arrangement as defined in claim 8, wherein said section is made of a different, firmly adhering, material than said ureter tube.

11. An arrangement as claimed in claim 1, wherein the outer shaft of the mandrin has a section of enlarged diameter having the form of a double cone tightly engaging a corresponding recess in the inner wall of the ureter tube in the proximal range of the ureter tube.

12. An arrangement as claimed in claim 1, wherein the outer shaft of the mandrin in the proximal section of the ureter tube has an external sleeve of elastic material firmly connected thereto, the outer wall of the external sleeve firmly engaging the inner wall of the ureter tube.

13. An arrangement as claimed in claim 12, wherein the mating surfaces of said mandrin and said sleeve are structured, and wherein said surfaces are fused with each other.

* * * * *